(12) United States Patent
Baxter-Jones

(10) Patent No.: US 11,154,236 B2
(45) Date of Patent: Oct. 26, 2021

(54) CERVIX MEASURING DEVICE AND METHOD

(71) Applicant: Rosalyn Baxter-Jones, Nashville, TN (US)

(72) Inventor: Rosalyn Baxter-Jones, Nashville, TN (US)

( * ) Notice: Subject to any disclaimer, the term of this patent is extended or adjusted under 35 U.S.C. 154(b) by 317 days.

(21) Appl. No.: 16/001,529

(22) Filed: Jun. 6, 2018

(65) Prior Publication Data

US 2018/0353120 A1    Dec. 13, 2018

Related U.S. Application Data

(60) Provisional application No. 62/516,297, filed on Jun. 7, 2017.

(51) Int. Cl.
*A61B 5/00* (2006.01)
*A61B 5/107* (2006.01)

(52) U.S. Cl.
CPC .......... *A61B 5/4331* (2013.01); *A61B 5/1076* (2013.01)

(58) Field of Classification Search
None
See application file for complete search history.

(56) References Cited

U.S. PATENT DOCUMENTS

| | | | | |
|---|---|---|---|---|
| 6,419,646 B1 * | 7/2002 | Baxter-Jones | ....... | A61B 5/1076 600/591 |
| 8,366,640 B2 * | 2/2013 | Bauer | ................. | A61B 5/1076 600/591 |
| 2002/0198471 A1 * | 12/2002 | Baxter-Jones | ....... | A61B 5/1076 600/591 |
| 2007/0100335 A1 * | 5/2007 | Fischer | ................ | A61B 18/149 606/45 |
| 2014/0266775 A1 * | 9/2014 | Moon | .................... | A61B 5/035 340/870.01 |
| 2016/0100861 A1 * | 4/2016 | Parys | .................... | A61B 17/42 600/249 |

* cited by examiner

*Primary Examiner* — Etsub D Berhanu
*Assistant Examiner* — Aurelie H Tu
(74) *Attorney, Agent, or Firm* — Parsons & Goltry; Robert Parsons; Michael Goltry

(57) ABSTRACT

A cervix measuring device is provided including an elongated shaft having a proximal end and a distal end, a positioning member slidably carried by the elongated shaft, the positioning member having a semicircular shape to allow partially encirclement of a base of a ectocervix, and a stop member stopping the positioning member from sliding past the distal end of the elongated shaft.

14 Claims, 4 Drawing Sheets

CERVIX MEASURING DEVICE AND METHOD

CROSS-REFERENCE TO RELATED APPLICATION

This application claims the benefit of U.S. Provisional Application No. 62/516,297, filed Jun. 7, 2017.

FIELD OF THE INVENTION

This invention relates to medical devices.

More particularly, the present invention relates to devices for measuring the length of the cervix.

BACKGROUND OF THE INVENTION

In the field of obstetrics, measurements taken of the cervix are important during pregnancies. Dimensions of the cervix at various times throughout a pregnancy are indicative of how the pregnancy is progressing. There are essentially four methods that can be used to evaluate the uterine cervix: digital examination, transabdominal ultrasound, transperineal ultrasound (TPS) and transvaginal sonography (TVS). Digital examination provides the most comprehensive evaluation of the cervix, assessing dilatation, position, consistency and length. However, this examination suffers from being subjective. The other types, while accurate, are expensive, require sophisticated equipment, and are time consuming. Recently, devices have been developed as a replacement for digital examination. These devices include rigid elongated elements inserted into the vagina to the base of the cervix. While effective, these devices require the use of a speculum to enable insertion of the device and viewing of the ectocervix to allow proper placement of the device. If the device is improperly positioned, the end of the device may be inadvertently inserted into the external os of the cervix. Inadvertent insertion of the end of the device into the external os can result in injury and damage. While less expensive than many current methods, the requirement of a speculum for use increases the time and expense of the procedure.

It would be highly advantageous, therefore, to remedy the foregoing and other deficiencies inherent in the prior art.

An object of the present invention is to provide a device for measuring a cervix without use of a speculum.

Another object of the present invention is to provide a cervix measuring device to assist in digital examination.

SUMMARY OF THE INVENTION

Briefly, to achieve the desired objects and advantages of the present invention provided is a cervix measuring device. The cervix measuring device includes an elongated shaft having a proximal end and a distal end, a positioning member slidably carried by the elongated shaft, the positioning member having a semicircular shape to allow partially encirclement of a base of a ectocervix, and a stop member stopping the positioning member from sliding past the distal end of the elongated shaft.

The positioning member can include a collar member slidably received on the elongated shaft. A first curved arm extends from the collar member in a first direction, and a second curved arm extends from the collar member in an opposing direction. The elongated shaft is formed of a flexible material being sufficiently flexible to deform and conform to the shape of an inserting hand and to the shape of a vagina in which it is inserted.

Also provided is a method of measuring a cervix. The method includes the step of providing a cervix measuring device including an elongated shaft having a proximal end and a distal end, a positioning member slidably carried by the elongated shaft, the positioning member having a semicircular shape, and a stop member stopping the positioning member from sliding past the distal end of the elongated shaft. The method further incudes the steps of positioning member proximate the distal end, conforming the elongated shaft to the shape of a hand and inserting the distal end and the positioning member of the cervix measuring device into a vagina using the hand. The positioning member is used to locate and partially encircle the ectocervix by feel. The cervix measuring device is then inserted until the distal end is placed against a vaginal wall adjacent the ectocervix, guided into position by the positioning member. Once properly positioned with the distal end against the vaginal wall adjacent the ectocervix, the position is maintained while moving the positioning member toward the proximal end until it is positioned adjacent the tip of the ectocervix.

BRIEF DESCRIPTION OF THE DRAWINGS

The foregoing and further and more specific objects and advantages of the invention will become readily apparent to those skilled in the art from the following detailed description of a preferred embodiment thereof, taken in conjunction with the drawings in which.

DETAILED DESCRIPTION OF A PREFERRED EMBODIMENT

Figure 1:
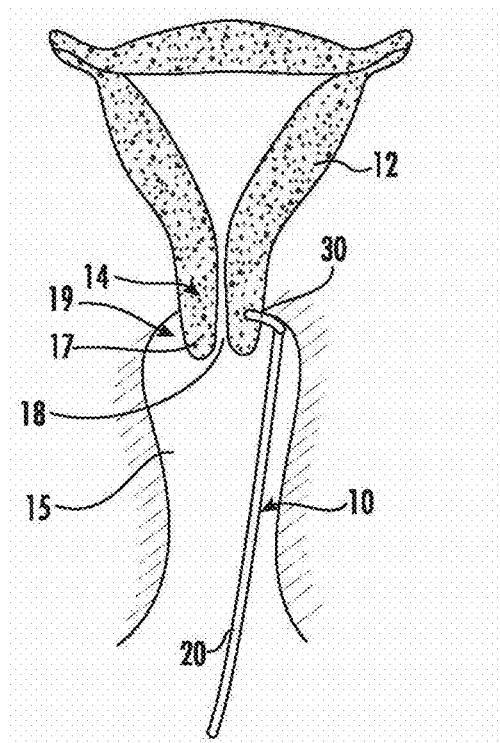
FIG. 1 is a simplified side view of a female reproductive system illustrating placement of a measuring device according to the present invention.

Turning now to the drawings in which like reference characters indicate corresponding elements throughout the several views, attention is directed to FIG. 1 which illustrates a cervix measuring device generally designated 10, positioned to take a measurement within a portion of a female reproductive system. The portions of the female reproductive system specifically illustrated include a uterus 12, a cervix 14 and a vagina 15. Vagina 15 is a canal that connects cervix 14 to the outside of a female body and through which device 10 extends. Cervix 14 is a cylinder-shaped neck of tissue that connects vagina 15 and uterus 12. Located at the lowermost portion of uterus 12, cervix 14 includes two main portions, an ectocervix 17, the part of cervix 14 that protrudes into vagina 15 and which can be seen from inside vagina 15 during a gynecologic examination, and an external os 18, an opening in the center of ectocervix 17. External os 18 opens to allow passage between uterus 12 and vagina 15. A fornix vaginae 19 is an area at the base of vagina 15 into which cervix 14 protrudes.

Cervix measuring device 10 is employed to measure the length of ectocervix 17. Stated another way, device 10 is used to measure the length of cervix 14 in the fornix vaginae. Also used herein, the term "fornix vaginae" refers to the recess formed between the vaginal wall and ectocervix 17. The fornix vaginae may be divided into pars anterior (the anterior fornix), the pars posterior (posterior fornix) and the pars lateralis (lateral fornix), depending on its relation to the walls of vagina 15. Measuring device 10 can be inserted into any of these parts of the fornix vaginae, depending on the choice of the user, to determine either the depth of the fornix vaginae at any particular point, or the length of ectocervix 17 in the fornix vaginae.

Figure 4:
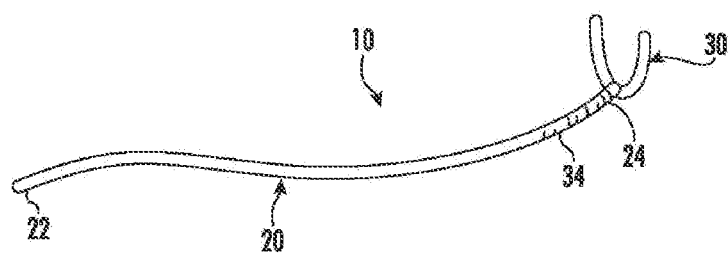
FIG. 4 is a perspective view of the measuring device of the present invention.

With additional reference to FIG. 4, measuring device 10 includes an elongated shaft 20 having a proximal end 22 and a distal end 24. For purposes of this description, proximal end 22 is the end of measuring device 10 proximate the user, and distal end 24 is the end of measuring device 10 first inserted into vagina 15. Elongated shaft 20 is preferably formed of a flexible material to permit manipulation thereof within vagina 15. Elongated shaft 20 can have substantially any cross-sectional shape, such as square, round, oval and the like, and is preferably formed of a biologically inert plastic material. While previous devices require the use of a speculum to enable insertion of the device and viewing of the ectocervix to allow proper placement of the device, the present invention is intended to be employed without the use of a speculum. By eliminating the use of a speculum, the cost of the procedure and the time involved for the procedure can be reduced. Without a speculum, a user inserts elongated shaft 20 into vagina 15 by feel alone. To insure proper placement of distal end 24, a positioning member 30 is slidably carried by shaft 20.

Figure 6:
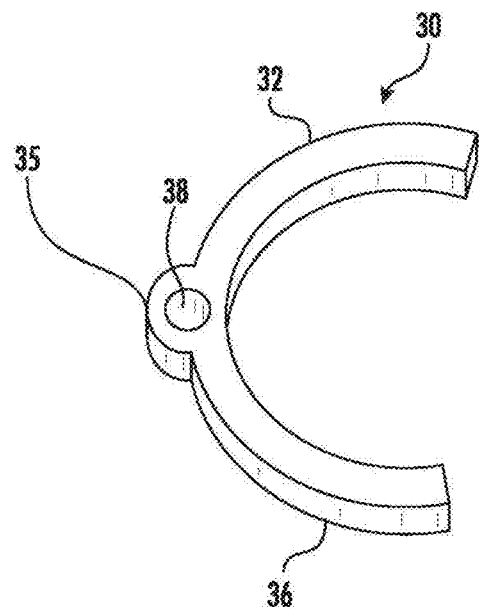
FIG. 6 is an enlarged perspective view of the positioning member of the measuring device.

With additional reference to FIG. 6, positioning member 30 has a curved or semicircular shape to allow it to partially encircle the base of ectocervix 17. A curved arm 32 extends from a collar member 35 in one direction, and a curved arm 36 extends from collar member 35 in an opposing direction. Collar member 35 includes an aperture 38 extending therethrough. Aperture 38 receives shaft 20 therethrough and provides the frictional engagement therewith. This semicircular shape ensures that distal end 24 is properly positioned to the side of ectocervix 17, and prevents any possibility of distal end inadvertently being inserted into external os 18. Inadvertent insertion of distal end into external os 18 can result in injury and damage.

Figure 2:
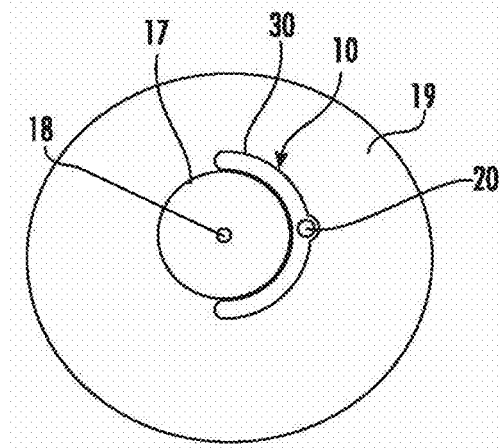
FIG. 2 is an enlarged top view of a portion of the female reproductive system shown in FIG. 1, illustrating proper placement of the measuring device.
Figure 3:
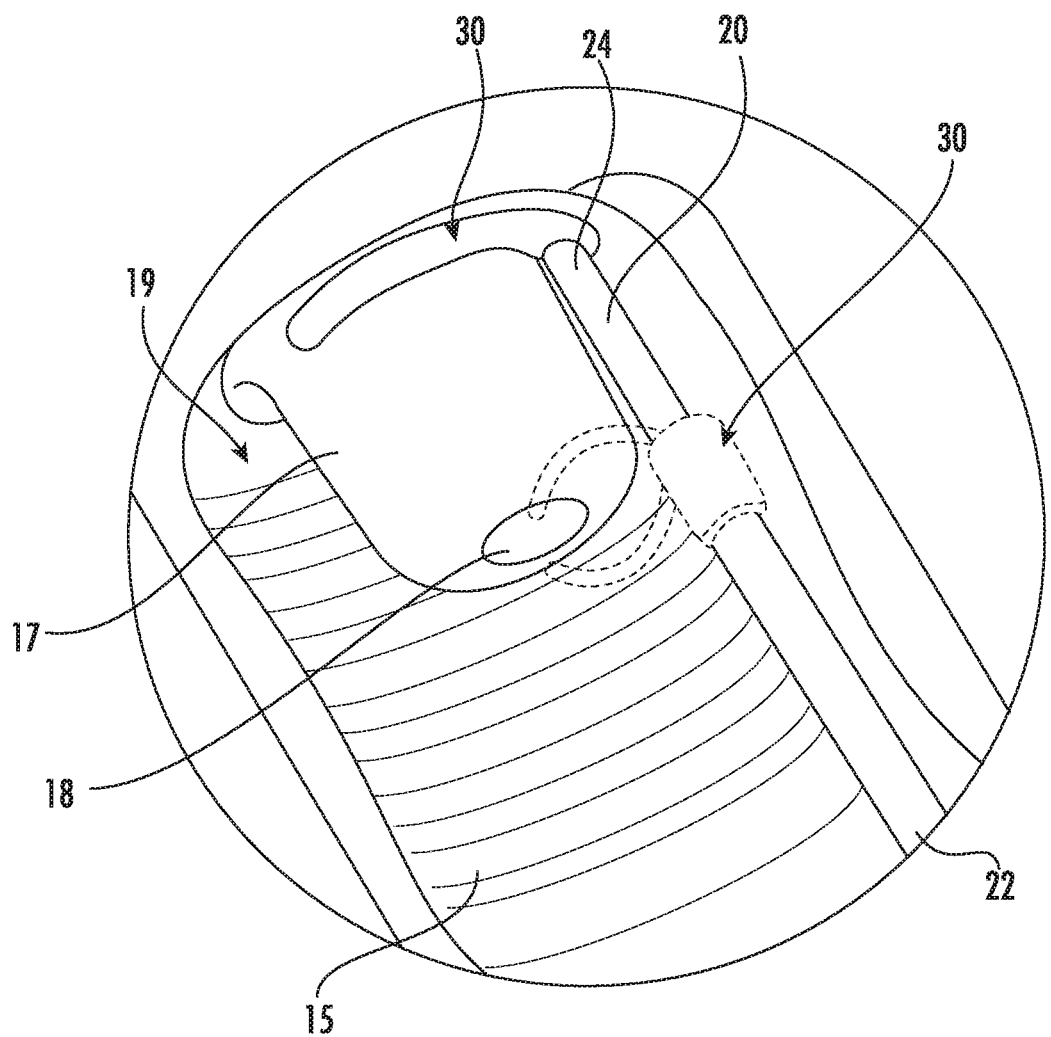
FIG. 3 is an enlarged perspective view of the initial placement of the measuring device proximate the ectocervix.
Figure 7:
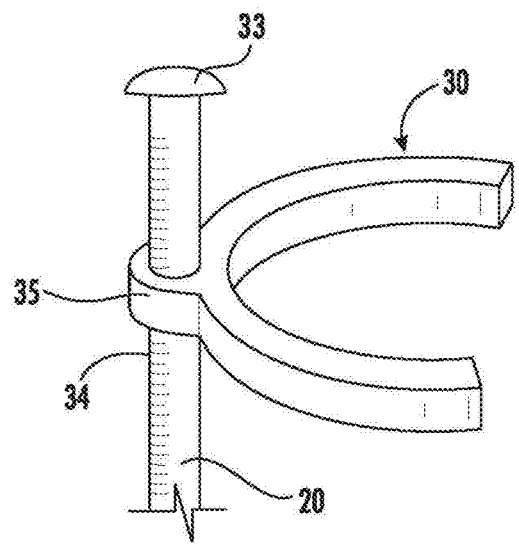
FIG. 7 is an enlarged view of the end of the measuring device showing the positioning member after a measurement.

Referring back to FIGS. 2 and 3, at the beginning of the procedure, positioning member 30 is positioned proximate distal end 24. As can be seen with momentary reference to FIG. 7, distal end 24 is preferably flattened to a button member 33, having slightly extending sides to provide non-abrasive contact to the vaginal wall, and to prevent positioning member 30 from sliding off shaft 20. It will be understood that while button member 33 is the preferred stop member of the present invention, a slight widening of distal end 24 and the like, can also be employed as a stop member to prevent positioning member 30 from being removed from distal end 24. Shaft 20 and positioning member 30 are then inserted into vagina 15 until button element 33 at distal end 24 is placed against the vaginal wall in the fornix vaginae adjacent ectocervix 17. Elongated shaft 20 is sufficiently flexible to permit insertion into, and conformation thereof to the shape of vagina 15. The flexibility of shaft 20 allows a user to insert distal end 24 along with a hand and fingers, with shaft 20 conforming to the shape of the hand and vagina 15. Since positioning of distal end 24 is not observable, positioning member 30 is used by feel to encircle ectocervix 17, properly positioning device 10. Once distal end 24 is positioned properly against the vaginal wall adjacent ectocervix 17, the user can slide positioning member 30 toward proximal end 22 until it is positioned adjacent the tip of ectocervix 17 (illustrated in broken line in FIG. 3). Positioning member 30 is then held in position by frictional engagement with shaft 20 or by a locking mechanism such as detents, clamps and the like. Device 10 is then withdrawn from vagina 15 and the distance between distal end 24 and positioning member 30 indicates the length of ectocervix 17 as shown in FIG. 7. Measuring indicia 34 can be carried by elongated shaft 20 proximate distal end 24 to provide a measuring scale.

Turning to FIGS. 6 and 7, positioning member 30 includes curved arms 32 and 36 extending outwardly from a collar 35. Collar 35 includes an aperture 38 therethrough for slidably receiving shaft 20. Collar 35 can include a friction engagement with shaft 20 which needs to be overcome to slidably position positionable member 30. A locking mechanism can be provided in the place of the simple friction arrangement. In a friction arrangement, positioning member 30 can be slidably moved along shaft 20 from distal end 24 toward proximal end 22. The movement caused by the user's fingers overcoming the friction between shaft 20 and positioning member 30. When positioning member 30 is positioned as desired, device can be removed with positioning device 30 held in position by friction. Various types of locking mechanism can also be employed. These include a clamp carried by collar 35 of positioning member 30 and releasably clampable to shaft 20, a deformable collar 35 which can be deformed inwardly against shaft 20 to prevent further movement, detents, or the like. The locking mechanism is movable between an engaged and a disengaged position, retaining positioning member 30 in position in the engaged position and allowing sliding movement of positioning member 30 in the disengaged position.

Figure 5:
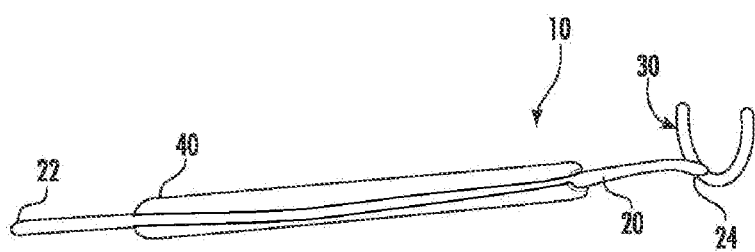
FIG. 5 is a perspective view of the measuring device of the present invention with stiffening cover.

Turning now to FIG. 5, measuring device 10 can be fitted with a stiffening cover 40. Stiffening cover 40 is a slotted tube in the preferred embodiment, which can be fitted over shaft 20 to render shaft 20 stiffer. This is an option that allows measuring device 10 to be used in combination with a speculum. When a speculum is employed, insertion of a hand directing distal end 24 is unnecessary. In this case, a visual position is possible. However, shaft 20 must be stiffened to allow positioning when grasping proximal end 22. Additionally, cover 40 can be slidably carried by shaft 20. In this manner, cover 40 can be grasped, and shaft 20 slidably manipulated as desired.

Various changes and modifications to the embodiments herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

1. A cervix measuring device comprising:
   an elongated shaft having a proximal end and a distal end;
   a positioning member slidably carried by the elongated shaft, the positioning member having a semicircular shape configured to partially encircle a base of an ectocervix at a juncture of the ectocervix with a vaginal wall; and a stop member stopping the positioning member from sliding past the distal end of the elongated shaft.

2. The cervix measuring device as claimed in claim 1 wherein the positioning member comprises:

a collar member slidably received on the elongated shaft;

a first curved arm extending from the collar member in a first direction; and a second curved arm extending from the collar member in an opposing direction to the first direction.

3. The cervix measuring device as claimed in claim 2 wherein the collar member includes an aperture extending therethrough, the aperture slidably receiving the elongated shaft therethrough.

4. The cervix measuring device as claimed in claim 1 further including a locking mechanism movable between an engaged position and a disengaged position, the locking mechanism retaining the positioning member when in the engaged position and allowing sliding movement of the positioning member when in the disengaged position.

5. The cervix measuring device as claimed in claim 1 wherein the positioning member is retained in position by frictional engagement with the elongated shaft.

6. The cervix measuring device as claimed in claim 1 wherein the elongated shaft is formed of a flexible material being sufficiently flexible to deform and conform to the shape of an inserting hand of a user and to the shape of a vagina in which it is configured to be inserted.

7. The cervix measuring device as claimed in claim 6 wherein the flexible material is formed of a biologically inert plastic material.

8. The cervix measuring device as claimed in claim 1 further including a stiffening cover fitted over the elongated shaft to render the elongated shaft less flexible than when the elongated shaft does not have the stiffening cover.

9. The cervix measuring device as claimed in claim 8 wherein the stiffening cover is a slotted tube slidably carried by the elongated shaft.

10. A method of measuring a cervix comprising the steps of:

providing a cervix measuring device including an elongated shaft having a proximal end and a distal end, a positioning member slidably carried by the elongated shaft, the positioning member having a semicircular shape configured to partially encircle a base of an ectocervix at a juncture of the ectocervix with a vaginal wall, and a stop member stopping the positioning member from sliding past the distal end of the elongated shaft;

positioning the positioning member proximate the distal end;

conforming the elongated shaft to the shape of a hand and inserting the distal end and the positioning member of the cervix measuring device into a vagina using the hand;

using the positioning member to locate and partially encircle the ectocervix;

continuing to insert the cervix measuring device until the distal end is placed against the vaginal wall adjacent the ectocervix; and maintaining the distal end against the vaginal wall adjacent the ectocervix while moving the positioning member toward the proximal end until it is positioned adjacent the inferior tip of the ectocervix.

11. The method as claimed in claim 10 further including the step of holding the positioning member in position by frictional engagement with the elongated shaft.

12. The method as claimed in claim 10 further comprising the step of providing the cervix measuring device with a locking mechanism movable between an engaged and a disengaged position, retaining the positioning member in position in the engaged position and allowing sliding movement of the positioning member in the disengaged position.

13. The method as claimed in claim 12 further including the step of holding the positioning member in position by engaging the locking mechanism.

14. The method as claimed in claim 10 further including the step of removing the cervix measuring device from the vagina and determining the height of the ectocervix by determining the distance between the positioning member and the distal end.

\* \* \* \* \*